(12) United States Patent
Tomura et al.

(10) Patent No.: US 7,875,749 B2
(45) Date of Patent: Jan. 25, 2011

(54) CLATHRATE HYDRATE CONTAINING QUATERNARY AMMONIUM SALT AS GUEST COMPOUND

(75) Inventors: Keiji Tomura, Tokyo (JP); Shingo Takao, Tokyo (JP); Takao Kitagawa, Tokyo (JP)

(73) Assignee: JFE Engineering Corporation, Tokyo (JP)

(*) Notice: Subject to any disclaimer, the term of this patent is extended or adjusted under 35 U.S.C. 154(b) by 0 days.

(21) Appl. No.: 12/584,494

(22) Filed: Sep. 3, 2009

(65) Prior Publication Data
US 2010/0004487 A1    Jan. 7, 2010

Related U.S. Application Data

(63) Continuation of application No. PCT/JP2008/053963, filed on Mar. 5, 2008.

(30) Foreign Application Priority Data

Mar. 6, 2007  (JP) .............. 2007-055262

(51) Int. Cl.
C07C 213/08 (2006.01)
C07C 211/62 (2006.01)
F17C 5/00 (2006.01)
F25D 5/00 (2006.01)

(52) U.S. Cl. ............. 564/281; 564/282; 564/291; 564/296; 62/4; 62/54.1; 62/114

(58) Field of Classification Search .......... None
See application file for complete search history.

(56) References Cited

U.S. PATENT DOCUMENTS 6,560,971 B2 * 5/2003 Takao et al. .......... 62/54.1

FOREIGN PATENT DOCUMENTS

| JP | 57-35224 | 2/1982 |
|---|---|---|
| JP | 60-195179-1 | 10/1985 |
| JP | 60-195179 A | 10/1985 |
| JP | 1-230690 A | 9/1989 |
| JP | 10-259978 | 9/1998 |
| JP | 11-35933 A | 2/1999 |
| JP | 11-80721 A | 3/1999 |
| JP | 11-351775 | 12/1999 |
| JP | 10-259978 | 10/2001 |
| JP | 2001-280875 | 10/2001 |
| JP | 2001-301884 | 10/2001 |
| JP | 2002-060739 A | 2/2002 |
| JP | 2002-263470 | 9/2002 |
| JP | 2004-3718 | 1/2004 |
| JP | 11-351775 | 11/2004 |
| JP | 2005-036060 A | 2/2005 |
| JP | 2005-126728 A | 5/2005 |
| JP | 2006-176674 A | 6/2006 |
| JP | 2007-246778 A | 9/2007 |
| WO | WO 2006/132322 A1 | 12/2006 |

OTHER PUBLICATIONS

Kawasaki Narike, et al., Application of a Gas Hydrate to a Cold Heat Storage Element, Chemical Engineering, vol. 27, No. 8, p. 603, Kagaku Kogyo, Aug. 1, 1982. Japan.
International Patent Application No. PCT/JP2006/311538 published WO/132322, Dec. 14, 2006.
Narike Kawasaki et. al, Application of a Gas Hydrate to a Cold Heat Storage Element, Chemical Engineering, Kagaku Kogyo, published Aug. 1, 1982 vol. 27, No. 8 p. 603, Table 1.
International Search Report PCT/ISA/210 for PCT/JP2008/053963, mailed May, 27, 2008, including English Translation.
International Search Report for WO 2006/132322 A1, mailed Sep. 19, 2006.
International Preliminary Report On Patentability issued by the International Bureau of WIPO on Sep. 29, 2009 in connection with International Application No. PCT/JP2008/053963.
Written Opinion of the International Searching Authority issued by the International Searching Authority (ISA/JP) on May 27, 2008 in connection with International Application No. PCT/JP2008/053963.

* cited by examiner

*Primary Examiner*—Brian J Davis
(74) *Attorney, Agent, or Firm*—John P. White; Cooper & Dunham LLP

(57) ABSTRACT

An aqueous solution containing a quaternary ammonium salt as a guest compound of a clathrate hydrate, having a property of producing the clathrate hydrate when cooled, and further containing a phosphate of an alkali metal added thereto. A clathrate hydrate produced by cooling an aqueous solution containing a quaternary ammonium salt and a phosphate of an alkali metal, wherein the quaternary ammonium salt is the guest compound.

5 Claims, No Drawings

CLATHRATE HYDRATE CONTAINING QUATERNARY AMMONIUM SALT AS GUEST COMPOUND

CROSS REFERENCE TO RELATED APPLICATIONS

This is a Continuation Application of PCT Application No. PCT/JP2008/053963, filed Mar. 5, 2008, which was published under PCT Article 21(2) in Japanese.

This application is based upon and claims the benefit of priority from prior Japanese Patent Application No. 2007-055262, filed Mar. 6, 2007, the entire contents of which are incorporated herein by reference.

BACKGROUND OF THE INVENTION

Field of the Invention

The present invention relates to techniques used to increase the heat storing rate of a latent heat storage agent or a clathrate hydrate usable as a component of a latent heat storage agent, and particularly to, for example, an aqueous solution having a property of producing a clathrate hydrate, a clathrate hydrate containing a quaternary ammonium salt as its guest compound and a slurry of a clathrate hydrate, a method for producing a clathrate hydrate and a method for increasing the rate of formation or growth of a clathrate hydrate and a method for preventing or limiting a super-cooling phenomenon which occurs when a clathrate hydrate is produced or grown.

In the present invention, the interpretation of the terms given below are as follows unless otherwise noted.

(1) The "clathrate hydrate" includes semi-clathrate hydrates.

(2) The "clathrate hydrate" may be abbreviated as "hydrate".

(3) The "guest compound" may be referred to as "guest".

(4) The term "slurry" means such a state that solid particles are dispersed or suspended in a liquid or a material put into that state. Though there is the case where a surfactant is added or mechanical stirring is carried out to put the solid particles which tend to be settled, sedimented or precipitated, into a floated state, any material may be called "slurry" as long as the solid particles are dispersed or suspended in the liquid. Any material in which the solid particles are dispersed or suspended unevenly is called "slurry" as long as the solid particles are dispersed or suspended in the liquid.

(5) The term "raw aqueous solution" means an aqueous solution containing the guest compound of a clathrate hydrate. Even if minute materials besides the guest compound are added or contained to the solution, this solution is also called "raw aqueous material". Also, if a clathrate hydrate is dispersed or suspended, any aqueous solution is called "raw aqueous solution" as long as it contains the guest compound of a clathrate hydrate.

(6) The term "hydrate forming temperature" means the equilibrium temperature at which the clathrate hydrate is to be formed or generated when the raw aqueous solution is cooled. Even in the case where the temperature at which the clathrate hydrate is formed is varied depending on the concentration of the guest compound of the raw aqueous solution, this temperature is called "hydrate forming temperature". It is to be noted that the "hydrate forming temperature" may be called "melting point" for the sake of convenience.

(7) The term "clathrate hydrate including, as its guest compound or guest compounds, at least one quaternary ammonium salt" may be abbreviated to "hydrate of quaternary ammonium salt" or "quaternary ammonium salt hydrate".

(8) The term "cold heat" means thermal energy ensuring a temperature higher than 0° C. and lower than 30° C. or thermal energy corresponding to that temperature. The term "cold heat range" means a temperature ranging higher than 0° C. and lower than 30° C. The term "cold storage" means the storage, accumulation or reservation of thermal energy generated by the clathrate hydrate having the hydrate forming temperature in the cold heat range.

(9) The term "heat storing property" means the property of being able to store, accumulate or reserve thermal energy. The property of being able to store, accumulate or reserve cold heat may be referred to as "cold heat storing property".

(10) The term "heat storage agent" means a material having a heat storing property regardless of the object and structure of storage, transportation and other objects and fields of applications of thermal energy. A material having a cold heat storing property may be referred to as "cold heat storage agent). A clathrate hydrate having the heat accumulation property may be used as a structural component of "heat storage agent" or "cold heat storage agent".

(11) The term "heat storage element" means a member having a heat storing property. The heat storage agent may be used as a structural element or component of "heat storage element". The term "cold heat storage element" means a member having a cold heat storing property. The cold heat storage agent may be used as a structural element or component of "cold heat storage element".

(12) The term "heat storing rate" means either the quantity of thermal energy which a unit volume or unit weight of a heat storage agent can store, accumulate or reserve in a unit time by a heat exchange operation in a certain condition, or a parameter having positive correlation with such quantity of the thermal energy.

(13) The term "harmonic melting point" means a temperature at which the concentration of the guest compound in the raw aqueous solution is equal to the concentration of the guest compound in the clathrate hydrate and therefore, the composition of the liquid phase is not changed before and after the clathrate hydrate is formed, when the clathrate hydrate is formed from the liquid phase of the raw aqueous solution.

In a phase diagram in which the ordinate is the hydrate forming temperature and the abscissa is the concentration of the guest compound in the liquid phase of the raw aqueous solution, the maximum point is the "harmonic melting point". Also, the concentration of the guest compound in the raw aqueous solution at which the harmonic melting point is given is called "harmonic melting point concentration". When the clathrate hydrate is formed from the raw aqueous solution having a concentration less than the harmonic melting point concentration, the concentration of the guest compound in the raw aqueous solution is dropped and the hydrate forming temperature with respect to the corresponding concentration is dropped.

Description of the Related Art

The clathrate hydrate is formed by cooling a raw aqueous solution to a temperature lower than the hydrate forming temperature and in this case, thermal energy corresponding to the latent heat is stored, accumulated or reserved in the crystal of the formed clathrate hydrate. The clathrate hydrate is therefore used as a latent heat storage agent or its component.

As an example of the above clathrate hydrate, a material containing a non-gas material as the guest compound, that is, a non-gas clathrate hydrate is known (Non-Patent Document 1). As a typical example of the non-gas clathrate hydrate, that including, as its guest compound, a salt containing quaternary ammonium is known (Patent Document 1).

Many a quaternary ammonium salt hydrate is formed at normal pressure, has a large latent heat at the time of formation and hence stores relatively large heat energy and also, is easily handlable because it is inflammable unlike paraffin.

Also, many a quaternary ammonium salt hydrate has a higher harmonic melting point or hydrate forming temperature than the melting point of ice (0° C. at normal pressure) and therefore, the temperature of a cooling medium used when a heat storage agent is cooled to form a hydrate may be higher, leading to a higher coefficient of performance (COP) of a refrigerating machine used to cool the cooling medium, which offers such an advantage as energy saving.

Moreover, many quaternary ammonium salt hydrates are easily dispersed or suspended in water or an aqueous solution, have generally a uniformly dispersed state, are reduced in coagulating ability, give rise to insignificant phase separation and are significantly reduced in fluid resistance. If each of these quaternary ammonium salt hydrates is formed in the form of a slurry (Patent Documents 2 and 3), a heat storage element, a heat storage agent, or a thermal transport medium may be structured and handled as a slurry (Patent Documents 4 and 5).

It may be therefore said that the quaternary ammonium salt hydrate is promising as a heat storage element, a heat storage agent or its structural element or structural component. Specific examples of the quaternary ammonium salt hydrate include aclathrate hydrate containing a tetra-n-butylammonium salt or tri-n-butyl-n-pentylammonium salt as the guest compound. It is known that a clathrate hydrate containing tetra-n-butylammonium bromide (TBAB) as the guest compound, in particular, includes a primary hydrate and a secondary hydrate which are different from each other in the number of hydrates (Patent Document 6).

Non-Patent Document 1: KAWASAKI Naritake and one other, "Application of a gas hydrate to a cold heat storage element", Chemical Engineering, Kagaku Kogyo, Aug. 1, 1982, Vol. 27, No. 8, p. 603, Table 1

Patent Document 1: Jpn. Pat. Appln. Publication No. 57-35224

Patent Document 2: Jpn. Pat. Appln. Unexamined Publication No. 2004-3718

Patent Document 3: Jpn. Pat. Appln. Unexamined Publication No. 2002-263470

Patent Document 4: Jpn. Pat. Appln. Unexamined Publication No. 10-259978

Patent Document 5: Jpn. Pat. Appln. Unexamined Publication No. 2001-301884

Patent Document 6: Jpn. Pat. Appln. Unexamined Publication No. 2001-280875

BRIEF SUMMARY OF THE INVENTION

Incidentally, when a heat storage agent is utilized, it may be preferred that the heat storing rate is higher. This is because, if the heat storing rate of the heat storage agent is higher, much thermal energy can be stored, accumulated or reserved in a shorter time, which affords a time to spare for the operation and allowances on technical specifications of heat storing type air conditioning equipment using a heat storage agent and assemblies, making it easy to design the equipment and assemblies, so that there are many cases of avoiding the complications of the structures, mechanisms and operations of the equipment and assemblies, leading to cost reduction. Therefore, it is desired to develop techniques for more increasing the heat storing rate of the heat storage agent.

On the other hand, in the case of storage, accumulation or reservation of latent heat when a clathrate hydrate is used as a heat storage agent, the heat storing rate closely relates to the formation and growth of a crystal of the clathrate hydrate. This is because the latent heat made by the clathrate hydrate is based on such a phenomenon that when a raw aqueous solution is cooled down to the hydrate forming temperature, a crystal of the clathrate hydrate having heat storing property is produced and grown.

Also, because the crystal of the clathrate hydrate has a complicated structure, the formation and growth of crystals are slower than those of ice. This means that the formation and growth of crystals of the clathrate hydrate determine the rate of heat storage of the clathrate hydrate. Therefore, in the case of intending to establish the techniques for improving the heat storing rate of the clathrate hydrate in the storage, accumulation or reservation of latent heat using the clathrate hydrate, there is a need for a method for more highly improving the behavior of the formation and growth of the crystal of the clathrate hydrate.

Also, when a raw aqueous solution is cooled to form a hydrate of a quaternary ammonium salt, a super-cooling phenomenon occurs in which no hydrate is produced even at a temperature lower than the hydrate forming temperature but the solution state is maintained at least temporarily when the raw aqueous solution is cooled at a certain cooling rate. This phenomenon retards the formation and growth of crystals of the hydrate and generally reduces the heat storing rate of a heat storage agent. For this reason, it is desired to develop a method for preventing or limiting the super-cooling phenomenon of the raw aqueous solution to avoid the reduction in heat storing rate or to more improve this heat storing rate.

Of course, the adverse influence of the super-cooling phenomenon is not limited to the reduction in heat storing rate. For example, if the super-cooling state of the raw aqueous solution is released unexpectedly, crystals of the clathrate hydrate are produced in a large amount and grown and there is the case where normal operations of the equipment and assemblies are disturbed. Therefore, the intention of preventing or limiting the super-cooling of the raw aqueous solution is not only to avoid the reduction in the heat storing rate of the clathrate hydrate.

Against the backdrop as above, when the clathrate hydrate is utilized as a latent heat storage agent or its component, some measures are taken including a method in which fine particles serving as cores for the formation of a hydrate are added to a raw aqueous solution, a method in which mechanical vibration is applied to the heating surface of a heat exchanger and a method in which a raw aqueous solution is stirred, to thereby prevent or limit the super-cooling phenomenon or to promote the release of super-cooling (see, for example, Patent Document 3).

However, when these measures are applied to the equipment and assemblies utilizing the clathrate hydrate as a latent heat storage agent or its component, this brings about the complications of the structures, mechanisms and operations of the equipment and assemblies, which is contrary to the need for cost reduction. Therefore, if the super-cooling phenomenon is desired to be limited or prevented, it is desirable to develop a method based on an idea as to the ingredients of the raw aqueous solution to cope with the above demand for cost reduction.

The present invention has been made in view of the above situation, and it is an object of the present invention to provide the techniques for improving the heat storing rate when a clathrate hydrate is used as a heat storage agent and the techniques for limiting and preventing super-cooling by adding a specified additive to an raw aqueous solution.

The inventors of the present invention have made earnest studies and as a result, found that if a phosphate of an alkali metal is added to a raw aqueous solution having the property of forming a hydrate of quaternary ammonium salt, the heat storing rate of a clathrate hydrate is increased when the raw aqueous solution is cooled to form the clathrate hydrate. The inventors of the present invention have also found that when a phosphate of an alkali metal is added to a raw aqueous solution having the property of forming a hydrate of quaternary ammonium salt, super-cooling which occurs when the raw aqueous solution is cooled to form the clathrate hydrate can be prevented or limited.

The present invention has been made based on these new findings and specifically are as follows.

An aqueous solution (raw aqueous solution) according to a first embodiment of the present invention comprises a quaternary ammonium salt as a guest compound of a clathrate hydrate, has a property of forming the clathrate hydrate by cooling, and contains a phosphate of an alkali metal added to the solution.

A clathrate hydrate according to a second embodiment of the present invention comprises a quaternary ammonium salt as a guest compound of a clathrate hydrate, and is formed by cooling an aqueous solution containing the quaternary ammonium salt and a phosphate of an alkali metal.

A slurry of a clathrate hydrate according to a third embodiment of the present invention comprises the clathrate hydrate according to the second embodiment of the present invention, dispersed or suspended in the aqueous solution.

A method for producing a clathrate hydrate according to a fourth embodiment of the present invention comprises preparing an aqueous solution containing a quaternary ammonium salt and a phosphate of an alkali metal; and forming a clathrate hydrate containing, as its guest compound, the quaternary ammonium salt by cooling the aqueous solution.

A method for increasing a rate of formation or growth of a clathrate hydrate according to a fifth embodiment of the present invention, wherein the clathrate hydrate containing, as its guest compound, a quaternary ammonium salt is formed or grown in an aqueous solution containing the quaternary ammonium salt, comprises preparing the aqueous solution to which a phosphate of an alkali metal is added; and cooling the aqueous solution to which the phosphate of the alkali metal is added.

A method for preventing or limiting a super-cooling phenomenon which occurs when a clathrate hydrate is produced or grown, according to a sixth embodiment of the present invention, wherein an aqueous solution containing a quaternary ammonium salt which is to be a guest compound of the clathrate hydrate is cooled to thereby produce the clathrate hydrate in the aqueous solution, comprises preparing an aqueous solution to which a phosphate of an alkali metal is added; and cooling the aqueous solution to which the phosphate of the alkali metal is added.

Typical examples of the phosphates of alkali metals in the present invention may include phosphates of sodium and phosphates of potassium and specific examples thereof include sodium dihydrogenphosphate, disodium hydrogenphosphate, trisodium phosphate, potassium dihydrogenphosphate, dipotassium hydrogenphosphate and tripotassium phosphate. Mixtures of these phosphates may be used. Also, in the present invention, typical examples of the quaternary ammonium salt include alkylammonium salts such as tetra-n-butylammonium salts.

According to the present invention, a phosphate of an alkali metal is added to a raw aqueous solution having the property of forming a hydrate of a quaternary ammonium salt, and therefore, the heat storing rate is increased when the raw aqueous solution is cooled to a temperature lower than the hydrate forming temperature to form the hydrate (hereinafter, called "heat storing rate increase effect").

Also, in the present invention, a phosphate of an alkali metal is added to a raw aqueous solution having the property of forming a hydrate of a quaternary ammonium salt, and therefore, the super-cooling phenomenon can be prevented or limited when the raw aqueous solution is cooled to a temperature lower than the hydrate forming temperature to produce the hydrate (hereinafter, called "super-cooling limiting effect").

To put it generally, the present invention produces at least one of the heat storing rate increase effect and super-cooling limiting effect.

The specific effect produced by each embodiment of the present invention is as follows.

According to the first embodiment of the present invention, a raw aqueous solution can be attained which has the property of forming a hydrate of a quaternary ammonium salt when it is cooled to a temperature lower than the hydrate forming temperature and can increase the heat storing rate of the hydrate when the hydrate is formed.

According to the first embodiment of the present invention, a raw aqueous solution can be attained which has the property of forming a hydrate of a quaternary ammonium salt when it is cooled to a temperature lower than the hydrate forming temperature and can prevent or limit the super-cooling phenomenon when the solution is cooled. These characteristics are preferable as the raw aqueous solution forming a clathrate hydrate used for a latent heat storage agent or its component.

According to the second embodiment of the present invention, a clathrate hydrate having a higher heat storing rate can be obtained. Also, a clathrate hydrate can be formed which is formed with the super-cooling being prevented and limited when the raw aqueous solution is cooled to a temperature lower than the hydrate forming temperature. These characteristics are suitable to the clathrate hydrate to be used for a latent heat storage agent or its component.

According to the third embodiment of the present invention, a slurry of the clathrate hydrate according to the second embodiment can be obtained. This slurry can be produced by cooling the raw aqueous solution according to the first embodiment to a temperature lower than the hydrate forming temperature, thereby making it possible to form and handle a heat storage element, a heat storage agent, and a thermal transfer medium.

According to the fourth embodiment of the present invention, a clathrate hydrate containing, as its guest compound, the above quaternary ammonium salt can be formed by cooling the aqueous solution containing the quaternary ammonium salt and a phosphate of an alkali metal, and therefore, at least one of the heat storing rate increase effect and super-cooling limiting effect is developed. As a result, the clathrate hydrate according to the second embodiment can be attained.

According to the fifth embodiment of the present invention, a clathrate hydrate containing, as its guest compound, the above quaternary ammonium salt can be formed by cooling the aqueous solution containing the quaternary ammonium salt and a phosphate of an alkali metal, and therefore, the techniques for increasing the rate of formation or growth of a hydrate of the above quaternary ammonium and for increasing generally the heat storing rate can be attained.

The increases in formation rate of a hydrate and in growth rate of a hydrate both contribute to the increase in the heat storing rate of the hydrate. Though the increase in formation rate necessarily more contributes to the increase in heat storing rate than the increase in growth rate from the viewpoint that the growth of the hydrate is premised on the formation of the hydrate, it may be the that the increase in growth rate contributes to an increase in heat storing rate from the viewpoint that the produced hydrate crystals become the cores of crystals when other crystals are produced.

According to the sixth embodiment of the present invention, a clathrate hydrate containing, as its guest compound, the above quaternary ammonium salt can be formed by cooling the aqueous solution containing the quaternary ammonium salt and a phosphate of an alkali metal, and therefore, the techniques can be attained which prevent and limit the super-cooling of the aqueous solution which occurs when the hydrate is formed.

DETAILED DESCRIPTION OF THE INVENTION

The present invention will be explained in detail by way of examples.

<Beaker Test for Formation of a Hydrate>

Sodium phosphate or potassium phosphate which is a typical example of an alkali metal phosphate was added in an aqueous solution of tetra-n-butylammonium bromide (TBAB) which is a typical example of a quaternary ammonium salt to examine the formation behavior and quantity of heat storage (or stored heat quantity) of the clathrate hydrate.

An aqueous solution containing 16 wt % TBAB was used as a blank of the raw aqueous solution. The hydrate forming temperature thereof was 7° C. or more and less than 9° C.

(Test Method)

A glass beaker equipped with a rotary stirring blade was charged with 90 g of the raw aqueous solution and dipped in or taken out from a 4° C. cooling liquid to thereby carry out a cooling operation or stop the cooling operation to observe the behavior of the formation of a clathrate hydrate.

Also, the formed clathrate hydrate was melted under heating by an electric heater provided in the glass beaker to measure accumulated calorie until the aqueous solution was heated to 12° C., thereby determining the stored heat quantity on a 12° C. basis. The reason why 12° C. is set to be the standard temperature is that a temperature at which the cooling medium is returned from the load side in a general central cooling air-conditioning system is 12° C. and the upper limit temperature in the temperature range when a heat storage agent or a heat transfer medium is used in a general central cooling air-conditioning system is 12° C., showing that the quantity of heat kept in a temperature range up to 12° C. is evaluated as the stored heat quantity.

COMPARATIVE EXAMPLE 1

Only TBAB Aqueous Solution

A glass beaker charged with an aqueous solution containing 16 wt % TBAB (room temperature) was dipped in a 4° C. cooling liquid and cooled while stirring the aqueous solution. When the temperature of the aqueous solution reached about 4° C. and 60 minutes passed, no hydrate was observed and super-cooling state was kept as it was.

COMPARATIVE EXAMPLE 2

A glass beaker charged with an aqueous solution containing 16 wt % TBAB (room temperature) was dipped in a 4° C. cooling liquid and cooled while stirring the aqueous solution. When the temperature of the aqueous solution reached 5.4° C., 1 g of the core of TBAB primary hydrate was poured as the core for formation of a hydrate. As the TBAB primary hydrate, one separately produced based on an aqueous solution containing 16 wt % TBAB was used.

The glass beaker was taken out of the cooling solution simultaneously when the above core was poured, whereby the cooling operation was temporarily stopped, and was retained for 2.5 minutes while continuing stirring. During this time, the aqueous solution exhibited a slurry state and a rise in a temperature of about 1 to 1.5° C. was measured. The reaction which can form a TBAB hydrate is an exothermic reaction. Therefore, the formation of the TBAB hydrate was confirmed from the confirmation of a general rise in temperature and visual observation of a slurry.

After the above retention for 2.5 minutes, the glass beaker was again dipped in the 4° C. cooling liquid and cooled for 3 minutes with stirring. Such a state that as the temperature of the slurry was gradually dropped, the concentration of the slurry was increased was observed visually.

After the above cooling for 3 minutes, the glass beaker was taken out of the cooling liquid to stop cooling though the stirring was continued. After the beaker was retained for one minute, the solution was heated at a constant power by an electric heater disposed in the glass beaker with stirring. The heating allowed the hydrate to melt so that the turbidity of the slurry was gradually lowered, resulting in the formation of an almost transparent aqueous solution. The aqueous solution was continuously heated until the temperature of the aqueous solution was further raised to reach 12° C.

The quantity of heat until the temperature of the aqueous solution reached 12° C. was calculated to find the stored heat quantity on a 12° C. basis. The stored heat quantity was 7.7 cal per 1 g of the aqueous solution.

COMPARATIVE EXAMPLE 3

The aqueous solution heated to 12° C. in Comparative Example 2 was further heated to 40° C. and cooled again.

Specifically, the glass beaker charged with the 40° C. aqueous solution was dipped in a 4° C. cooling solution to cool the aqueous solution with stirring. When the aqueous solution was cooled to about 4° C. and 60 minutes passed, the formation of a hydrate was not observed.

In Comparative Example 2, the TBAB primary hydrate was poured as the core for the formation of a hydrate. However, it was confirmed that the hydrate was melted when heated to 12° C. and that it did not function as the hydrate forming core in the second cooling operation.

EXAMPLE 1

(TBAB Aqueous Solution with 2 wt % of Dipotassium Hydrogenphosphate Added Thereto)

Dipotassium hydrogenphosphate was added to the aqueous solution containing 16 wt % TBAB in an amount of 2 wt % based on the weight of the aqueous solution to prepare a raw aqueous solution.

A glass beaker charged with the above aqueous solution (room temperature) was dipped in a 4° C. cooling liquid and cooled while stirring the aqueous solution. When the temperature of the aqueous solution reached 5.4° C., 1 g of TBAB primary hydrate was poured as the core for formation of a hydrate. As the TBAB primary hydrate poured as the core, one separately produced based on an aqueous solution containing 16 wt % TBAB was used.

The time taken until the temperature of the aqueous solution reached 5.4° C. (namely, the cooling rate) was the same as that of Comparative Example 2.

The glass beaker was taken out of the cooling solution simultaneously when the above core was poured, whereby the cooling was temporarily stopped, and was retained for 2.5 minutes while continuing stirring. During this time, the aqueous solution exhibited a slurry state and a rise in temperature was measured. The formation of the TBAB hydrate was confirmed from the confirmation of a rise in temperature and visual observation of a slurry.

A rise in temperature since the core was poured to release the super-cooling was about 1.5 to 2° C. and was larger by about 0.5° C. than that of Comparative Example 2. Also, the rate of a rise in temperature was larger than that of Comparative Example 2.

After the above retention for 2.5 minutes, the glass beaker was again dipped in the 4° C. cooling liquid and cooled for 3 minutes with stirring. Such a state that as the temperature of the slurry was gradually dropped, the concentration of the slurry was increased was observed visually.

After the above cooling for 3 minutes, the glass beaker was taken out of the cooling liquid to stop cooling though the stirring was continued. After the beaker was retained for one minute, the solution was heated at a constant power by an electric heater disposed in the glass beaker with stirring. The heating allowed the hydrate to dissolve so that the turbidity of the slurry was gradually lowered, resulting in the formation of an almost transparent aqueous solution. The aqueous solution was continuously heated by the electric heater until the temperature of the aqueous solution was further raised up to 12° C.

The quantity of heat until the temperature of the solution reached 12° C. was calculated to find the stored heat quantity on a 12° C. basis. The stored heat quantity was 8.1 cal per 1 g of the aqueous solution. The stored heat quantity was more increased by 0.4 cal per 1 g of the aqueous solution than that of Comparative Example 2 and the increase in the stored heat quantity corresponded to an increase of about 5%.

Here, the stored heat quantity of Example 1 which was more increased than that of Comparative Example 2 will be investigated.

When the specific heat of the raw aqueous solution of Example 1 was measured, a change due to the addition of 2 wt % of dipotassium hydrogenphosphate was not confirmed. Also, each solubility of dipotassium hydrogenphosphate and hydrate of dipotassium hydrogenphosphate was so large that no precipitate was produced in the cooling and heating conditions of Example 1. Therefore, even though the influence of dipotassium hydrogenphosphate itself on the stored heat quantity of the hydrate of TBAB is small, it is admitted that the stored heat quantity of the hydrate of TBAB was increased in Example 1.

As mentioned above, the addition of dipotassium hydrogenphosphate ensured that the increase in the quantity of heat until the aqueous solution reached 12° C., and specifically, the increase in the heat storing quantity of the TBAB hydrate in the series of cooling processes could be attained and therefore, the rate of heat storage or heat storing rate could be improved or increased.

Also, the increase in the rise of temperature (specifically, the increase in the amount of the hydrate to be produced) and the increase in the rise rate of temperature after the release of super-cooling show that the rate of formation of the TBAB hydrate was increased by addition of dipotassium hydrogenphosphate.

EXAMPLE 2

(TBAB Aqueous Solution with 1 wt % of Disodium Hydrogenphosphate Added Thereto)

A test was made in the same manner as in Example 1 except that 1 wt % of disodium hydrogenphosphate was added instead of adding 2 wt % of dipotassium hydrogenphosphate in Example 1.

The time taken until the temperature of the aqueous solution reached 5.4° C. (namely, the cooling rate) was the same as that of Comparative Example 2.

While the cooling was temporarily stopped simultaneously when the core was poured and the glass beaker was retained, the aqueous solution exhibited a slurry state and a rise in temperature was measured. The formation of the TBAB hydrate was confirmed from visual observation of a slurry and the confirmation of a rise in temperature. A rise in temperature since the core was poured to release the super-cooling was about 1.5 to 2° C., which was larger by 0.5° C. than that of Comparative Example 2. Also, the rate of a rise of temperature was larger than that of Comparative Example 2.

The quantity of heat until the temperature of the solution reached 12° C. was calculated to find the stored heat quantity on a 12° C. basis. The stored heat quantity was 8.1 cal per 1 g of the aqueous solution. The stored heat quantity was more increased by 0.4 cal per 1 g of the aqueous solution than that of Comparative Example 2 and the increase in the stored heat quantity corresponded to an increase of about 5%.

Here, the stored heat quantity of Example 2 which was more increased than that of Comparative Example 2 will be investigated.

When the specific heat of the raw aqueous solution of Example 2 was measured, a change due to the addition of 1 wt % of disodium hydrogenphosphate was not confirmed. Also, each solubility of disodium hydrogenphosphate and hydrate of disodium hydrogenphosphate was so large that it produced no precipitate in the cooling and heating condition of Example 2. Therefore, even though the influence of disodium hydrogenphosphate itself on the stored heat quantity of the hydrate of TBAB is small, it is admitted that the stored heat quantity of the hydrate of TBAB was increased in Example 2.

As mentioned above, the addition of 1 wt % of disodium hydrogenphosphate ensured that the increase in the quantity of heat until the aqueous solution reached 12° C., and specifically, the increase in the stored heat quantity of the TBAB hydrate in the series of cooling processes could be attained and therefore, the rate of heat storage or heat storing rate could be improved or increased.

Also, the increase in the rise of temperature (specifically, the increase in the amount of the hydrate to be produced) and the increase in the rise rate of temperature after the release of super-cooling show that the rate of formation of the TBAB hydrate was increased by addition of disodium hydrogenphosphate.

EXAMPLE 3

(TBAB Aqueous Solution with 3 wt % of Disodium Hydrogenphosphate Added Thereto)

Disodium hydrogenphosphate was added to the aqueous solution containing 16 wt % TBAB in an amount of 3 wt % based on the weight of the above aqueous solution to prepare a raw aqueous solution. In this Example 3, the core for the formation of a hydrate was not poured.

A glass beaker charged with the raw aqueous solution (room temperature) was dipped in a 4° C. cooling liquid and cooled while stirring the aqueous solution. When the temperature of the aqueous solution was about 7° C., a rise in the temperature of the aqueous solution was measured, and when the cooling operation was continued and the temperature of the aqueous solution reached 5° C., a second rise in temperature was measured. The second rise in temperature occurred within 10 minutes since the aqueous solution having room temperature was started to be cooled.

When the second rise in temperature was observed, the aqueous solution exhibited a slurry state to admit the formation of TBAB hydrate.

Specifically, it was found that in the case of the raw aqueous solution prepared by adding 3 wt % of disodium hydrogenphosphate in the TBAB aqueous solution in the same manner as in Example 3, the release of super-cooling could be attained without such a specific operation for releasing super-cooling as to pour the TBAB primary hydrate as the core for the formation of a hydrate. When, like the case of Comparative Example 1, 60 minutes passed, a thick slurry was produced and the temperature of the slurry was almost 4° C. The quantity of heat required to heat the solution to 12° C. was more than twice that of Comparative Example 1.

In this manner, the addition of 3 wt % of disodium hydrogenphosphate ensured that the increase in the quantity of heat until the aqueous solution reached 12° C., and specifically, the increase in the heat storing quantity of the TBAB hydrate in the series of cooling processes could be attained and therefore, the rate of heat storage or heat storing rate could be improved or increased.

EXAMPLE 4

Using the raw aqueous solution (the TBAB aqueous solution to which 3 wt % of disodium hydrogenphosphate was added) of Example 3, the test involving repetitive heating and cooling operations was made.

After the test of Example 3 was made, the aqueous solution obtained after it was heated to 40° C. was again cooled.

Specifically, the glass beaker charged with the aqueous solution having a temperature of 40° C. was dipped in a 4° C. cooling liquid to cool the aqueous solution with stirring. As a result, the super-cooling was released and the formation of a hydrate was confirmed with increase in temperature, when the aqueous solution was about 5 to 7° C.

Thereafter, after the same aqueous solution was heated to 12° C., it was cooled and this operation was repeated. Similarly, the release of the super-cooling was observed at about 5 to 7° C.

It was found that in the case of the raw aqueous solution obtained by adding 3 wt % of disodium hydrogenphosphate to the TBAB aqueous solution, the release of the super-cooling could be attained without such a specific operation for releasing the super-cooling as to pour the TBAB primary hydrate as the core for the formation of a hydrate.

EXAMPLE 5

(13 wt % TBAB Aqueous Solution with 9 wt % of Dipotassium Hydrogenphosphate Added Thereto)

Dipotassium hydrogenphosphate was added to the aqueous solution containing 13 wt % TBAB in an amount of 9 wt % based on the weight of the aqueous solution to prepare a raw aqueous solution.

A glass beaker charged with the above aqueous solution (room temperature) was dipped in a 4° C. cooling liquid and cooled while stirring the aqueous solution. When the temperature of the aqueous solution reached 5.4° C., 1 g of TBAB primary hydrate was poured as the core for formation of a hydrate to release super-cooling. As the TBAB primary hydrate poured as the core, one separately produced based on an aqueous solution containing 16 wt % TBAB was used.

The time taken until the temperature of the aqueous solution reached 5.4° C. (namely, the cooling rate) was almost the same as that of Comparative Example 2.

The glass beaker was taken out of the cooling solution simultaneously when the above core was poured, whereby the cooling operation was temporarily stopped, and was retained for 2.5 minutes while continuing stirring. During this time, the aqueous solution exhibited a slurry state and a rise in temperature was measured. The formation of a hydrate was confirmed from visual observation of a slurry and the confirmation of a rise in temperature.

A rise in temperature since the core was poured to release the super-cooling was about 3 to 4° C. and was larger by about 2.5° C. than that of Comparative Example 2. Also, the rate of rise in temperature was larger than that of Comparative Example 2.

After the above retention for 2.5 minutes, the glass beaker was again dipped in the 4° C. cooling liquid and cooled for 3 minutes with stirring. Such a state that as the temperature of the slurry was gradually dropped, the concentration of the slurry was increased was observed visually.

After the above cooling for 3 minutes, the glass beaker was taken out of the cooling liquid to stop cooling though the stirring was continued. After the beaker was retained for one minute, the solution was heated at a constant power by an electric heater disposed in the glass beaker with stirring. The heating allowed the hydrate to melt so that the turbidity of the slurry was gradually lowered, resulting in the formation of an almost transparent aqueous solution. The aqueous solution was continuously heated by the electric heater until the temperature of the aqueous solution was further raised up to 12° C.

The quantity of heat until the temperature of the solution reached 12° C. was calculated to find the stored heat quantity on a 12° C. basis. The stored heat quantity was 10.1 cal per 1 g of the aqueous solution. The stored heat quantity was more increased by 2.4 cal per 1 g of the aqueous solution than that of Comparative Example 2 and the increase in the stored heat quantity corresponded to an increase of about 31%.

When the specific heat of the raw aqueous solution of Example 5 was measured, a change due to the addition of 9 wt % of dipotassium hydrogenphosphate to the aqueous solution of 13% TBAB was not confirmed. Also, each solubility of dipotassium hydrogenphosphate and hydrate of dipotassium hydrogenphosphate was so large that no precipitate was produced in the cooling and heating conditions of Example 5. Therefore, it may be said that even though the influence of dipotassium hydrogenphosphate itself on the stored heat quantity is small, the rate of formation of the hydrate derived from TBAB was increased and the stored heat quantity of the hydrate of TBAB was increased in Example 5.

COMPARATIVE EXAMPLE 4

A test was made in the same manner as in Comparative Example 2 except that an aqueous solution of 13 wt % TBAB was used in place of the aqueous solution of 16 wt % TBAB. As a result, the stored heat quantity on a 12° C. basis was lower than that of Comparative Example 2.

As shown in Example 5, the aqueous solution of 13 wt % TBAB to which 9 wt % dipotassium hydrogenphosphate was added was more remarkably increased in heat accumulation and particularly, the rate of heat storage on a 12° C. basis could be more improved or increased than the aqueous solution of 16 wt % TBAB of Comparative Example 2 though the concentration of TBAB in this Example was lower.

This means that the amount of TBAB required to obtain a desired stored heat quantity can be relatively reduced by addition of dipotassium hydrogenphosphate.

The amount of expensive quaternary ammonium salt required to obtain a clathrate hydrate, its slurry and a latent heat storage agent containing this clathrate hydrate having the same stored heat quantity can be relatively reduced by adding such an inexpensive alkali metal phosphate.

Accordingly, a clathrate hydrate, its slurry and a latent heat storage agent containing this clathrate hydrate having the same stored heat quantity can be attained at lower costs and the economy of techniques using these materials can be improved.

What is claimed is:

1. An aqueous solution which comprises a quaternary ammonium salt as a guest compound of a clathrate hydrate, and has a property of producing the clathrate hydrate by cooling, wherein a phosphate of alkali metal is added to the solution to increase a heat storing rate of the clathrate hydrate, said phosphate of alkali metal being at least one selected from the group consisting of sodium dihydrogenphosphate, disodium hydrogenphosphate, trisodium phosphate, potassium dihydrogenphosphate, dipotassium hydrogenphosphate and tripotassium phosphate.

2. A clathrate hydrate product formed by cooling a raw aqueous solution containing a quaternary ammonium salt and a phosphate of alkali metal which is at least one phosphate of alkali metal selected from the group consisting of sodium dihydrogenphosphate, disodium hydrogenphosphate, trisodium phosphate, potassium dihydrogenphosphate, dipotassium hydrogenphosphate and tripotassium phosphate, said clathrate hydrate product comprising a clathrate hydrate containing the quaternary ammonium salt as a guest compound and having an increased heat storing rate, and the phosphate of alkali metal.

3. A slurry of a clathrate hydrate product, which comprises the clathrate hydrate product dispersed or suspended in a raw aqueous solution, said the clathrate hydrate product comprising a clathrate hydrate containing a quaternary ammonium salt as a guest compound and having an increased heat storing rate, and is formed by cooling the raw aqueous solution containing the quaternary ammonium salt and a phosphate of alkali metal which is at least one phosphate of alkali metal selected from the group consisting of sodium dihydrogenphosphate, disodium hydrogenphosphate, trisodium phosphate, potassium dihydrogenphosphate, dipotassium hydrogenphosphate and tripotassium phosphate.

4. A method for producing a clathrate hydrate, comprising:
preparing an aqueous solution containing a quaternary ammonium salt and a phosphate of alkali metal; and
forming a clathrate hydrate containing, as its guest compound, the quaternary ammonium salt by cooling the aqueous solution to increase a heat storing rate of the clathrate hydrate.

5. A method for increasing a rate of formation or growth of a clathrate hydrate, wherein the clathrate hydrate containing, as its guest compound, a quaternary ammonium salt is formed or grown in an aqueous solution containing the quaternary ammonium salt, the method comprising:
preparing an aqueous solution containing the quaternary ammonium salt to which a phosphate of an alkali metal is added; and
cooling the aqueous solution to which the phosphate of the alkali metal is added, to form the clathrate hydrate containing, as its guest compound, the quaternary ammonium salt.

* * * * *